(12) United States Patent
Velasco

(10) Patent No.: US 9,194,869 B2
(45) Date of Patent: Nov. 24, 2015

(54) METHOD FOR EVALUATING THE SENSITIVITY AND SPECIFICITY OF FAST MALARIA-DIAGNOSIS TEST KITS

(75) Inventor: Nancy Arrospide Velasco, Lima (PE)

(73) Assignee: INSTITUTO NACIONAL DE SALUD, Lima (PE)

( * ) Notice: Subject to any disclaimer, the term of this patent is extended or adjusted under 35 U.S.C. 154(b) by 0 days.

(21) Appl. No.: 14/360,112

(22) PCT Filed: Nov. 25, 2011

(86) PCT No.: PCT/PE2011/000006
§ 371 (c)(1),
(2), (4) Date: Jul. 30, 2014

(87) PCT Pub. No.: WO2013/077751
PCT Pub. Date: May 30, 2013

(65) Prior Publication Data
US 2014/0356883 A1    Dec. 4, 2014

(51) Int. Cl.
*G01N 33/53*    (2006.01)
*G01N 33/569*    (2006.01)

(52) U.S. Cl.
CPC .... *G01N 33/56905* (2013.01); *G01N 2333/445* (2013.01); *G01N 2333/904* (2013.01); *G01N 2333/988* (2013.01)

(58) Field of Classification Search
CPC .................................................. G01N 33/56905
See application file for complete search history.

(56) References Cited

U.S. PATENT DOCUMENTS

2002/0086820 A1 *    7/2002    Rosen et al. ................... 514/12

* cited by examiner

*Primary Examiner* — Albert Navarro
(74) *Attorney, Agent, or Firm* — Abelman, Frayne & Schwab

(57) ABSTRACT

The invention relates to a method for evaluating kits for rapid diagnosis of malaria, in order to determine or to test the sensitivity and specificity thereof. To that end, the reactive strips of the diagnostic kits are exposed to different concentrations of the malaria parasite in a method that allows data on sensitivity and specificity indicated on the technical sheet of the kit to be ascertained.

1 Claim, No Drawings

METHOD FOR EVALUATING THE SENSITIVITY AND SPECIFICITY OF FAST MALARIA-DIAGNOSIS TEST KITS

CROSS-REFERENCE TO RELATED APPLICATIONS

This application is a National Phase of PCT/PE2011/000006, filed 25 Nov. 2011, which claims priority from the PCT Application, the disclosure of which is incorporated herein by reference.

TECHNICAL FIELD

This invention is in the technical field of assessment methods used for the fast diagnosis kit immunochromatographic Malaria, checking its sensitivity.

OBJECT OF THE INVENTION

A laboratory method for testing the sensitivity and specificity of immunochromatographic fast diagnostic kits for malaria.

BACKGROUND OF THE INVENTION

Current Situation

"Malaria" is an endemic disease in approximately 80% of departments of Peru and even in several geographic areas of Latin America and Central America. Control of this epidemic requires health ministry programs in each country aimed at curbing the disease in its different strategies: clinical diagnosis, laboratory diagnosis, entomological vector control, treatment, preventive promotional work.

Health surveillance and control of malaria is worldwide for microscopic diagnosis of malaria through the implementation of the thick film, which is sensitive, specific, economical and is not complex in its procedures so it is considered as the main benchmark. Since the invention of immunochromatographic fast diagnosis tests by the nineties, there is another alternative of diagnosis laboratory in malaria: the commonly known as "fast tests for malaria diagnosis" through immunochromatographic diagnostic kit; basically, these are biologically compound of monoclonal antibody type that have the ability to recognize highly specific antigenic fractions on the parasite being able to discriminate different species involved in malaria cases. This diagnosis is particularly relevant in malaria for its diagnostic sensitivity, requiring only a few minutes for the test execution, ability to run several tests in the same time and finally it does not require microscopes, so it is recommended by the World Health Organization WHO for its use in geographically remote malariagens areas and lack of resources for microscopic diagnosis.

Fast tests for malaria diagnosis offered in the commercial market are numerous and have different biological basis which decreases or increases its diagnostic sensitivity as applicable, by which is REQUIRED to be first evaluated laboratory with positive and negative benchmark typical of each region or country, this due to antigenic variability that parasite populations of genus *Plasmodium* arise. The second moment of assessment of these tests is on the same epidemiological stage where the endemy shows with samples of malaragens patients both assessments provide the most proximate result to a real sensitivity and specificity submitted in these kits, or fast tests; so both evaluations are needed before health authorities of any country decide to control malaria with these kits.

Analysis Problem-Solution (Invention)

There is no similar evaluation protocol with all the herein described sequential methodology employed and that solve the evaluation of fast malaria in vitro tests (laboratory) prior to be used in patient diagnosis.

This is a laboratory method (Method of Evaluation) that carried out in the manner proposed solves the problem to know the sensitivity of fast tests regarding their ability to detect the disease (Malaria) before these can be compared in large quantities by the Ministries of Health or the governments concerned, for its endowment and massive use in field work for diagnosis and control of malaria.

The laboratory method described herein has been structured considering all the conditions to show that the method is valid within the parameters of acceptances ie. semiqualitative methods diagnostic laboratory:
SENSITIVITY from 95% to 100%
SPECIFICITY between 95% to 100%
ACCURACY reaches Kappa 1
LIMIT OF DETECTION detects at the lower limit a parasitaemia up to 100p/ul (parasites per microliter).

The method detects fast malaria test involving detection of HRP-II protein core of the PLDH isoenzyme aldolase or the combination of these molecules.

The method for the evaluation of immunochromatographic "kits" for diagnosis of malaria caused by *Plasmodium vivax* and *P. falciparum* and thus determine its specificity and sensitivity; includes the following phases:

a) Random sampling of the kits in stock.

b) The preparation of the blood sample of the patient with the disease that will be used to evaluate the kit (the patient must live in the endemic area where the kits will be used to be evaluated with this method), which in turn includes:

i Taking a blood sample from a patient who has the disease clinically and laboratory diagnosis has not less than ++ and comes from an endemic area, the sample must be available for testing at a maximum of 48 hrs. of being taken, not hemolyzed samples are accepted.

ii Determine the concentration of parasitemia of the sample (i) by the thick film method for determine the concentration of $\rho/\mu l$ blood.

iii preparing a set of dilutions called "panel" in which serum dilutions are made from the sample described in (i) and whose initial concentration has been determined in phase (ii), to achieve parasitemia ($\rho/\mu l$) desired for the test (dilutions can be repeated to achieve the desired density), concentrations in this panel must be in the range of 100-5000 p/ul hematic sample.

iv treatment of uncomplicated falciparum malaria, who/htm/rbm/2003.50 pag.29)

c) Finally, do react as indicated in the commercial kit, dilutions of blood samples prepared in (b) with inmunocromatics strips of the kit to verify the sensitivity and specificity. For this, assay must be duplicated in parallel and running blind is antigen-antibody reaction (hematic-strip shown) by inserting a strip into a cryovial individually.

Advantages of the Invention

To insert in the assay positive controls prepared "in house" with circulating samples in regions makes it a better way to evaluate the real antigenic sensitivity that contains a particular malaria diagnostic kit.

It is simple to implement in their steps, does not require expensive equipment or supplies that are not in the commercial market for laboratory products.

DETAILED DESCRIPTION OF INVENTION

The invention refers to a method for evaluating the immunochromatographic "kits" for diagnosis of malaria caused by *Plasmodium vivax* and *P. falciparum*, and thus determine its specificity and sensitivity; including the following steps:

a) Random sampling of the kits in stock.

b) The preparation of the blood sample of the patient with the disease that will be used to evaluate the kit (the patient must live in the endemic area where the kits will be used to be evaluated with this method), which in turn includes:

i Taking a blood sample from a patient who has the disease clinically and laboratory diagnosis has not less than ++ and comes from an endemic area, the sample must be available for testing at a maximum of 48 hrs. of being taken, not hemolyzed samples are accepted.

ii Determine the concentration of parasitemia of the sample (i) by the thick film method for determine the concentration of $\rho/\mu l$ blood.

iii preparing a set of dilutions called "panel" in which serum dilutions are made from the sample described in (i) and whose initial concentration has been determined in phase (ii), to achieve parasitemia ($\rho/\mu l$) desired for the test (dilutions can be repeated to achieve the desired density), concentrations in this panel must be in different ranges:

100 p/ul
500 p/ul
1000 p/ul
5000 p/ul

Each concentration will be on an aliquot, from lowest to highest concentration and by species: *P. falciparum* and *P. vivax*.

Aliquots are accommodated on the rack in vertically, covering first column one, then the two, followed by three, etc.

The minimum value included is 100 p/ul~and the maximum 5,000 p/ul.

TABLE 1

Limit of detection of the assessment test kit
THE LOWER LIMIT OF DETECTION is 100/parasites per microliter.

| Parasites by miaolitro p/ul | 100 | 500 | 1000 | 5000 |
|---|---|---|---|---|
| Sensib % | 100 | 100 | 100 | 100 |
| Specif % | 100 | 100 | 100 | 100 |

All necessary equipments were calibrated. The temperature and humidity of the laboratory was controlled by a thermo hygrometer.

A check of the concentrations of the panel by counting parasithemy in thick blood parasites per microliter of blood. Finally, reacting as indicated in the commercial kit, dilutions of the blood sample prepared in (b) with inmunocromatics strips kit to verify the sensitivity and specificity. For this assay must be done in duplicate in parallel and running blind is antigen-antibody reaction (heffi ^sample).

As stated lines before, the method includes several phases and following the considerations outlined in performing each of said phases:

Diagnostic Kits Sampling:

Diagnostic kits samples that are individualized to date, to be considered in sampling, must be in their original packaging and unopened containers and must be transported and stored according to manufacturer specifications.

The selection of the lot is performed according to Standards Sampling Plans, the number of larger containers is obtained by applying Table Mil-STD 105 D per attribute, simple type, inspection level II and for the sample selection Simple Random Method is applied (PRT-CNCC-003. Sampling of pharmaceutical and related products). The process for obtaining diagnosis kits samples and legal counter sample is recorded in a Sampling Act (FOR-003 sampling PRT-CNCC-003. Sampling Act CNCC).

Sampled Diagnosis Kits are Distributed as Follows:

To evaluate the sensitivity and specificity of the kit, the number of kits required to Malaria Laboratory of the CNSP (National Center for Public Health of Peru) are delivered.

Legal counter samples (second group of Kits) are reserved in custody in the NCCC (National Center for Quality Control of the National Health Institute from Health Ministry of Peru).

This step must be executed in this way at the National Health Institute because the SERVICE will be provided by CNCC and CNSP will participate only as a service provider.

Then to determine how many kits (individual sachets) will be tested in positive, negative and different densities of parasite load, it proceeds with the sampling by simple affixation. Diagnosis kits are labeled according to a table of random numbers for the three groups of evaluation:

*Plasmodium vivax*
*Plasmodium falciparum*
Negative samples.

Preparation for positive and negative samples to be used in the evaluation of the kit.

Positive samples are obtained by volume of 5 ml. by venipuncture into vacuum tubes with EDTA anticoagulant, from patients with positive clinical diagnosis of malaria by *P. vivax* or *P. falciparum* whose density is not less than two crosses (++), using the semi qualitative scoring method in crosses for diagnosis of Malaria. (Manual of Laboratory procedures for the diagnosis of Malaria. Standards Technical Series No 39. Uma 2003).

For either case (*P. vivax* and *P. falciparum*), the sample is obtained from the malaria infected patients before initiating treatment.

Negative samples are also obtained by venipuncture into vacuum tubes with EDTA from clinically healthy persons, negativity is confirmed through a Test of Thick Film through microscopic observation to endorse him as a person without Malaria.

Samples hemolyzed are not accepted for test.

Carriage Conditions of Samples Taken:

Positive blood samples are obtained in endemic areas of malaria by *P. vivax* and *P. falciparum* and transported by the analyst, the place where the test is performed by maintaining the cold serie at 2° C. to 8° C.

Carriage conditions of samples are realized under bio-security standards for the transportation of samples.

Transportation is executed in bio-security containers validated for 72 h at temperatures from 2° C.-8° C.

Samples should reach the laboratory where the assay sample is executed in a period no longer than 48 h from obtained the sample.

Conservation of Positive and Negative Samples Until the Time of the Evaluation Process:

Blood samples are maintained in refrigeration (2° C.-8° C.), until the time of the assay.

Assay must be executed only until 48 hours after taking the samples, otherwise the parasites lose viability.

Biosecurity Conditions:

The staff responsible for obtaining fresh blood sample must be specially trained and instructed in operations related to his work and must follow the instructions of the Laboratory Biosafety Manual (MPR-CNSP-012-INS) regarding safety practices in obtaining blood samples and use of personal protective equipment (apron, mask, gloves).

The analysts responsible for the evaluation of sensitivity and specificity of fast tests for the diagnosis of malaria must be trained in operations related to their work and meet the standards of biosecurity related and relevant.

Preparation of Dilutions of the Sample for Evaluation Kits:
Preparation of Positive and Negative Samples "in House":
Once the result of parasite density per microliter of blood parasites is obtained, we proceed to perform the calculations for the dilution of the blood sample in the density of parasitemia in the range requested by the client.

Once known the density parasite value of the parasitized sample, is brought to the desired dilution executing a sample dilution of negative control, using the formula:

$$V_1 \times C_1 = V_2 \times C_2$$

Where:
$V_1$=Volume No 1.
$C_i$=Concentration No 1.
$V_2$=Volume No 2.
$C_2$=concentration No 2.

Then, adjust the parasitemia by microscopic examination of thick blood film, expressing its value in parasite/ul and following the method of calculating the number of parasites per microliter of blood. Formula for calculating ul blood parasites in blood smear:

Nr. parasites×6000=Parasites/ul
Nr. leucocyte

Nr. parasites: number of parasites counted in thick blood
Nr. leucocyte: number of leucocytes counted in thick blood
ul: microliter In case the concentration achieved is not the desired, dilution is repeated until the desired density corroborating parasites quantitative counts per microliter of blood.

Distribution of samples with different parasite load of both species in the evaluation panel.

Run this procedure vertically starting in column 1, according to the following distribution scheme.

TABLE 2

Panel shows "In house" positive and negative evaluation of fast tests for malaria diagnosis
1 2 3 4 5 6 7 8

| | | | | | | | |
|---|---|---|---|---|---|---|---|
| pf | pv | pv | pf | pf | pv | pv | pf |
| 100 p/ul | 1000 p/ul | 100 p/ul | 1000 p/ul | 100 p/ul | 1000 p/ul | 100 p/ul | 1000 p/ul |
| pf | pv | pv | pf | pf | pv | pv | pf |
| 500 p/ul | 5000 p/ul | 500 p/ul | 5000 p/ul | 500 p/ul | 5000 p/ul | 500 p/ul | 5000 p/ul |
| neg | neg | neg | neg | neg | neg | neg | neg |
| pf | pf | pv | pv | pf | pf | pv | pv |
| 1000 p/ul | 100 p/ul | 1000 p/ul | 100 p/ul | 1000 p/ul | 100 p/ul | 1000 p/ul | 100 p/ul |
| pf | pf | pv | pv | pf | pf | pv | pv |
| 5000 p/ul | 500 p/ul | 5000 p/ul | 500 p/ul | 5000 p/ul | 500 p/ul | 5000 p/ul | 500 p/ul |
| neg | neg | neg | neg | neg | neg | neg | neg |
| pv | pf | pf | pv | pv | pf | pf | pv |
| 100 p/ul | 1000 p/ul | 100 p/ul | 1000 p/ul | 100 p/ul | 1000 p/ul | 100 p/ul | 1000 p/ul |
| pv | pf | pf | pv | pv | pf | pf | pv |
| 500 p/ul | 5000 p/ul | 500 p/ul | 5000 p/ul | 500 p/ul | 5000 p/ul | 500 p/ul | 5000 p/ul |
| neg | neg | neg | neg | neg | neg | neg | neg |

NAV
pf = *P. falciparum*
pv = P.wVox
neg = negative
p/ul = parasites per microliter Concentrations of parasitemia of samples that will be used in the panel for the evaluation should be 100, 500, 1000 and 5000 p/ul, which must be duly adjusted and confirmed in terms of its density, as previously explained, these are the samples that will be arranged in cryovials, in order to introduce the strip from the kits to be evaluate.

Concentration in the panel should not exceed 5000 p/ul, because for experimental experience it has been observed that higher concentrations produce an inhibition of reaction Ag-Ab.

In the panel is not considered a lower concentration to 100 p/ul, since the Ag-Ab test, were not reactive under parasite densities in blood samples. However, it should have a concentration of 100 p/ul intended to ensure that commercial kits evaluated, always ensure high sensitivity and ability to detect low densities in patients suffering from malaria, regardless of the behavior of the disease worldwide.

Duplicate testing parallel and blind by two analysts who will execute the antigen-antibody reaction (hematic-strip sample) by inserting a strip from the kit under evaluation in a cryovial one by one to reach the calculated sample size executed and according to what indicates the insert of the test that is being processed.

For each container that represents a concentration of parasites per microliter of blood has a result of the reaction in the strip. This gives a first drop and strip result panel from Analyst one and a second panel of results for the analyst two.

TABLE 3

Results from Analyst One
Positive and negative "in house" sample panel for the
evaluation of fast tests for malaria diagnosis
RESULTS FROM ANALYST ONE
A B C D E F G H

| A | B | C | D | E | F | G |
|---|---|---|---|---|---|---|
| pf | pv | pv | pf | pf | pv | pv |
| 100 p/ul | 1000 p/ul | 100 p/ul | 1000 p/ul | 100 p/ul | 1000 p/ul | 100 p/ul |
| 1 = f | 10 = V | 19 = V | 28 = F | 37 = F | 46 = V | 55 = V |
| pf | pv | pv | pf | pf | pv | pv |
| 500 p/ul | 5000 p/ul | 500 p/ul | 5000 p/ul | 500 p/ul | 5000 p/ul | 500 p/ul |
| 2 = F | 11 = V | 20 = V | 29 = F | 38 = F | 47 = V | 56 = V |
| neg | neg | neg | neg | neg | neg | neg |
| 3 = N | 12 = N | 21 = N | 30 = N | 39 = N | 48 = V | 57 = N |
| pf | pf | pv | pv | pf | pf | pv |
| 1000 p/ul | 100 p/ul | 1000 p/ul | 100 p/ul | 1000 p/ul | 100 p/ul | 1000 p/ul |
| 4 = F | 13 = F | 22 = V | 31 = V | 40 = F | 49 = V | 58 = V |
| pf | pf | pv | pv | pf | pf | pv |
| 5000 p/ul | 500 p/ul | 5000 p/ul | 500 p/ul | 5000 p/ul | 500 p/ul | 5000 p/ul |
| 5 = F | 14 = F | 23 = V | 32 = V | 41 = F | 50 = F | 59 = V |
| neg | neg | neg | neg | neg | neg | neg |
| 6 = N | 15 = N | 24 = N | 33 = N | 42 = N | 51 = N | 60 = N |
| pv | pf | pf | pv | pv | pf | |
| 100 p/ul | 1000 p/ul | 100 p/ul | 1000 p/ul | 100 p/ul | 1000 p/ul | |
| 7 = V | 16 = F | 25 = F | 34 = V | 43 = V | 52 = F | |
| pv | pf | pf | pv | pv | pf | |
| 500 p/ul | 5000 p/ul | 500 p/ul | 5000 p/ul | 500 p/ul | 5000 p/ul | |
| 8 = V | 17 = F | 26 = F | 35 = V | 44 = V | 53 = F | |
| neg | neg | neg | neg | neg | neg | |
| 9 = N | 18 = N | 27 = N | 36 = N | 45 = N | 54 = N | | pf = *P. falciparum*
pv = *P. Vivox*
neg = negative
p/ul = parasites per microliter

TABLE 4

Results from Analyst two.
Positive and negative "in house" sample Panel for the
evaluation of fast tests for malaria diagnosis
RESULTS FROM ANALYST TWO
A B C D E F G H

| A | B | C | D | E | F | G |
|---|---|---|---|---|---|---|
| pf | pv | pv | pf | pf | pv | pv |
| 100 p/ul | 1000 p/ul | 100 p/ul | 1000 p/ul | 100 p/ul | 1000 p/ul | 100 p/ul |
| 61 = f | 70 = V | 79 = V | 88 = F | 97 = F | 106 = V | 115 = V |
| pf | pv | pv | pf | pf | pv | pv |
| 500 p/ul | 5000 p/ul | 500 p/ul | 5000 p/ul | 500 p/ul | 5000 p/ul | 500 p/ul |
| 62 = F | 71 = V | 80 = V | 89 = F | 98 = F | 107 = V | 116 = V |
| neg | neg | neg | neg | neg | neg | neg |
| 63 = N | 72 = N | 81 = N | 90 = N | 99 = N | 108 = V | 117 = N |
| pf | pf | pv | pv | pf | pf | pv |
| 1000 p/ul | 100 p/ul | 1000 p/ul | 100 p/ul | 1000 p/ul | 100 p/ul | 1000 p/ul |
| 64 = F | 73 = F | 82 = V | 91 = V | 100 = F | 109 = V | 118 = V |
| pf | pf | pv | pv | pf | pf | pv |
| 5000 p/ul | 500 p/ul | 5000 p/ul | 500 p/ul | 5000 p/ul | 500 p/ul | 5000 p/ul |
| 65 = F | 74 = F | 83 = V | 92 = V | 101 = F | 110 = F | 119 = V |
| neg | neg | neg | neg | neg | neg | neg |
| 66 = N | 75 = N | 84 = N | 93 = N | 102 = N | 111 = N | 120 = N |
| pv | pf | pf | pv | pv | pf | |
| 100 p/ul | 1000 p/ul | 100 p/ul | 1000 p/ul | 100 p/ul | 1000 p/ul | |
| 67 = V | 76 = F | 85 = F | 94 = V | 103 = V | 112 = F | |
| pv | pf | pf | pv | pv | pf | |
| 500 p/ul | 5000 p/ul | 500 p/ul | 5000 p/ul | 500 p/ul | 5000 p/ul | |
| 68 = V | 77 = F | 86 = F | 95 = V | 104 = V | 113 = F | |
| neg | neg | neg | neg | neg | neg | |
| 69 = N | 78 = N | 87 = N | 96 = N | 105 = N | 114 = N | | pf = *P. falciparum* NAV
pv = *P. vivax*
neg = negative
p/ul = parasites per microliter These results obtained are entered into 2×2 contingency tables stats in which a rate of sensitivity and specificity of 100% should be find, as an indicator that the kit is efficient.

TABLE 5

Evaluation of sensitivity and specificity

|  |  | Gota Gruesa | | |
|---|---|---|---|---|
|  |  | Positivo (con Malaria) | Negativo (sin Malaria) | Total |
| pLDH | Positivo | a | b | a + b |
|  | Negativo | c | d | c + d |
|  | Total | a + c | b + d |  |

Specificity is Calculated by the Following Formula:

$E = \dfrac{d}{b+d}$ $E = -100\%$

The Sensitivity is Calculated by the Following Formula:

$S = \dfrac{a}{a+c}$ $S = 100\%$

Sensitivity and specificity of the analyst one is evaluated.

TABLE 6

Contingency table for two by two for sensitivity and specificity evaluation for Analyst ONE.
FIG. 2 Tabla de contingencia de dos por dos para evaluacion se Sensibilidad y especiificidad

|  |  | Gota Gruesa | | |
|---|---|---|---|---|
|  |  | Positivo (con Malaria) | Negativo (sin Malaria) | Total |
| Prueba Rapids | Positivo | 40 | 0 | 40 |
|  | Negativo | 0 | 20 | 20 |
|  | Total | 40 | 20 | 60 |

|  |  | Gota Gruesa | | |
|---|---|---|---|---|
|  |  | Positivo (con Malaria) | Negativo (sin Malaria) | Total |
| Prueba Rapids | Positivo | 40 | 0 | 40 |
|  | Negativo | 0 | 20 | 20 |
|  | Total | 40 | 20 | 60 |

Sensitivity and specificity of the analyst two is evaluated.

TABLE 7

Contingency table for two by two for sensitivity and specificity evaluation for Analyst TWO.
FIG. 2 Contingency table for two by two for sensitivity and specificity evaluation

|  |  | Gota Gruesa | | |
|---|---|---|---|---|
|  |  | Positivo (con Malaria) | Negativo (sin Malaria) | Total |
| Prueba Rapids | Positivo | 40 | 0 | 40 |
|  | Negativo | 0 | 20 | 20 |
|  | Total | 40 | 20 | 60 |

Specificity Calculated Gave the Following Value:

$IE = 100\%$

Sensitivity Calculated Gave the Following Value:

$Is = 100\% I$

The ACCURACY of the method is evaluated by the Kappa index which is an statistic in which the strength agreement of the results of the two analysts according to the following assessment is measured:

K Value Force Concordance
<0.20 Poor
0.21 to 0.40 Weak
0.41 to 0.60 Moderate
0.61 to 0.80 Good
0.81-1.00 Very good The lower limit of detection of parasitemia including 100 p/ul is identified and for the upper limit is considered 5000 p/ul (parasites per microliter).

Technology sector referred to or applied the invention.

The invention applies in the health sector, specifically for the evaluation of kits for fast diagnosis of malaria.

A DESCRIPTION OF A BETTER WAY TO IMPLEMENT OR EXECUTE THE INVENTION

Sampling for Diagnostic Kit Phase:

Samples of diagnostic kits that are individualized to date, to be considered in sampling, must be in their original packaging and unopened containers and must be transported and stored according to manufacturer specifications.

The selection of the lot is performed according Sampling Plan Standards, ISO 2859-1 PERUVIAN STANDARD TECHNIQUE Table I—code letter size sample page. 21 of 78.

With this table according to the size of lots entered as a general inspection level II the code letter will be obtained.

This code letter is located in the following table named Table II A—Single sampling plans for normal inspection. In this table the code letter is located in the column: Code letter of the size of the sample and see the sample size related.

For the sample selections the Simple Random Method is applied: Sampling of pharmaceutical products and related CNCC PRT-lera-AMU-001 $1^{st}$. edition, p 2003-01-15 page 13 of 22.

Sampled diagnostic kits are distributed as follows:

To evaluate the sensitivity and specificity of the kit, the number of kits required are delivered by the Laboratory where the assay will be executed, in this case the Malaria Laboratory of the National Centre of Public Health, National Institute of Health CNSP-INS.

Legal counter samples (second group of Kits) are reserved in custody in the case of the National Institute of Health in Peru for example, in the National Control Center CNCC. This second group of samples is important because after doing the test may be a discrepancy with the results from customers who ordered assess Kits, then in that case we proceed to use the second set of kits to run back to the assay.

Finally, to determine how many kits (individual sachets) are to be tested in positive, negative and different densities of parasite load, proceed with statistical sampling by simple affixation.

The invention claimed is:

1. A method for random sampling of commercial immunochromatographic kits to determine their specificity and sensitivity for the fast diagnosis of *Plasmodium vivax* and *Plasmodium falciparum*, which comprises the steps of:

a) preparing a blood sample of a patient from an area endemic to *p. vivax* and *p. falciparum*, which comprises:
  i) taking a blood sample from a patient who has been found to have malaria by virtue of a laboratory and clinical diagnosis of not less than ++;
  ii) determining the concentration of parasitemia of the blood sample in i) by the thick film method for determining the concentration of p/µL blood;
  iii) preparing a dilution panel, wherein serum dilutions are made from the blood sample in i) and whose initial concentration has been determined in ii) to achieve the parasitemia (p/µL) desired for the test concentration from about 100 to about 5000 p/µL of the blood sample;

verifying the concentrations of said dilution panel by the thick drop method for diagnosing malaria; and reacting the blood sample dilutions prepared in a) with an immunochromatic strip in each of the commercial kits to verify the sensitivity and specificity of each kit in the diagnosis of malaria.

* * * * *